United States Patent [19]

Kurtz et al.

[11] Patent Number: 4,516,430
[45] Date of Patent: May 14, 1985

[54] ECONOMICAL TRANSDUCER APPARATUS FOR USE IN THE MEDICAL FIELD

[75] Inventors: Anthony D. Kurtz, Teaneck; Timothy A. Nunn, Ridgewood; Joseph R. Mallon, Franklin Lakes, all of N.J.

[73] Assignee: Kulite Semiconductor Products, Inc., Ridgefield, N.J.

[21] Appl. No.: 558,033

[22] Filed: Dec. 5, 1983

[51] Int. Cl.³ .............................................. G01L 1/22
[52] U.S. Cl. ..................... 73/727; 128/675; 338/4
[58] Field of Search .................. 73/726, 727, DIG. 4, 73/720, 721; 338/4; 361/283; 128/675; 310/338; 357/26

[56] References Cited

U.S. PATENT DOCUMENTS

| | | | |
|---|---|---|---|
| 3,868,719 | 2/1975 | Kurtz et al. | 357/26 |
| 3,951,707 | 4/1976 | Kurtz et al. | 156/630 |
| 4,023,562 | 5/1977 | Hynecek | 73/727 |
| 4,216,404 | 8/1980 | Kurtz et al. | 357/26 |
| 4,314,225 | 2/1982 | Tominaga et al. | 73/727 |

Primary Examiner—Donald O. Woodiel
Attorney, Agent, or Firm—Arthur L. Plevy

[57] ABSTRACT

There is disclosed a medical transducer apparatus which employs composite planar members each of which is fabricated from a highly insulative material. The members are positioned in congruency and a first member which may be a composite member has a diaphragm area located on the surface thereof to which a piezoresistive gage is bonded. The gage is surrounded by an aperture in another member to enable leads from the gage to be directed to an interconnection and circuit board also fabricated from an insulator material. The structure provides isolation to the patient in regard to the biasing source used for the gage array and also provides isolation based on external voltage which serves to protect the transducer during operation.

20 Claims, 6 Drawing Figures

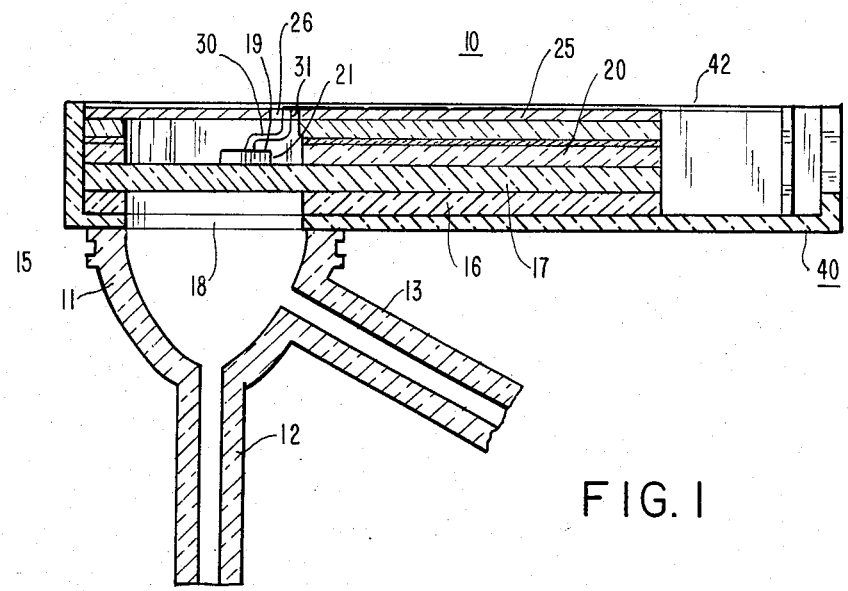
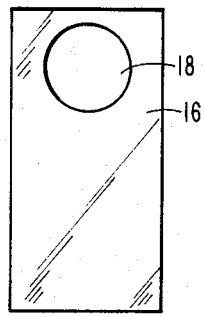
FIG. 2
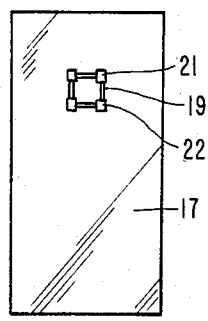
FIG. 3
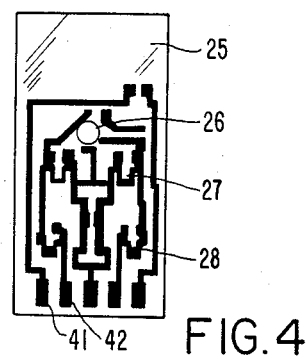
FIG. 4
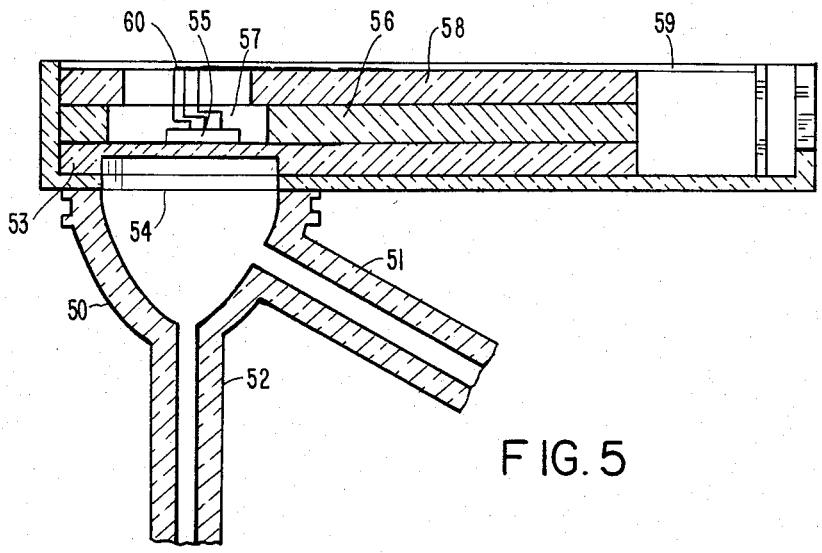
FIG. 5
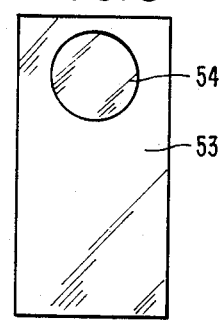
FIG. 6

ECONOMICAL TRANSDUCER APPARATUS FOR USE IN THE MEDICAL FIELD

BACKGROUND OF THE INVENTION

This invention relates to electromechanical transducers in general and more particularly to a transducer particularly adapted for use in the medical field.

Transducers have been employed in the medical field for quite some time. A very common type of transducer consists of resistive transducer elements which can be excited by AC or DC current. As such the transducers are commonly employed for the monitoring of blood pressure by use of catheters or a direct puncture technique. The type of transducers employed include bonded and unbonded strain wire bridges as well as silicon and piezoresistive elements.

The use of such transducers for monitoring blood pressure has substantially increased, and, therefore, it is apparent that there is a need for an economical unit. There is a further need to develop a unit which is readily compatible with electronic patient monitors which exist in the hospital. This relates to fabricating a transducer which has standard outputs in regard to its terminals so that the device can be utilized with conventional monitoring equipment found in a hospital. Although the application of pressure transducers for the measurement of blood pressure is most common, the same transducers can be used in many cases for the measurement of other fluid coupled physiological pressures such as intracranial, gastroenterological, uterine and bladder pressure. It is thus apparent that there is a need for an economical and reliable transducer which can operate in the various environments.

In any event, the use of a catheter or a direct puncture technique employing a transducer introduces a possible conductive pathway directly from the transducer to the heart of the patient. In view of the fact that such transducers are commonly employed with patients who may require defribillation with equipment generating voltages of 10,000 volts, it is important that such a transducer be well insulated both for patient safety and transducer serviceability. Although the conductivity of this pathway is significantly lower than that of other types of electrodes, it is necessary that the transducer be isolated or insulated to avoid any additional risk to the patient.

Apart from the above problems, is the problem of the continuous expansion of pressure measurement by the use of transducers and the fact that these measurements are conducted in a variety of locations throughout the hospital. Each of these locations within the same hospital may be supplied with different patient monitoring equipment. This fact necessitates that the hospital stock a large number of transducers made by various manufacturers to assure the availability of replacement devices for each specific monitor. Additional transducers must be kept on hold due to the use of gas sterilants which require significant aeration time. Also, as a patient is moved within the hospital, new transducers may have to be drawn from supply in order to accommodate the different pieces of equipment. At each point, the plumbing must be disconnected, the new transducer reconnected and the system flushed and debubbled. This procedure significantly affects the accuracy of the measurement and may contaminate the liquid column thus presenting an infection hazard to the patient, as well as being costly and inconvenient.

Apart from the above considerations, there remains the typical problem regarding handling and abuse of the transducer. Essentially based on many considerations, the transducers have to be relatively rugged in order to withstand large forces which may occur if they are dropped or otherwise mishandled.

Based on the nature of the field, presently there are a host of manufacturers which supply transducers of various configurations and operating characteristics for use in medical electronics. The devices presently supplied have various disadvantages which relate to the above noted problems. It is, therefore, an object of the present invention to provide an electrical medical transducer which is reliable and which provides electrical isolation for patient use.

It is a further object of the present invention to provide a medical transducer which is extremely rugged while capable of reliable operation with repeatable characteristics.

BRIEF DESCRIPTION OF THE PREFERRED EMBODIMENT

A pressure transducer apparatus particularly adapted for use in inplementing pressure measurements in the medical field comprising a first planar member fabricated from a first highly insulative material and having on a surface a given area adapted to deflect upon application of a force thereto, a hemispherical hollow member having an opened bottom and a domed surface with said opened bottom coupled about said given area of said first planar member, with said hemispherical member having at least one pressure port extending from said domed surface and communicating with said hollow, a piezoresistive sensor member secured to said first planar member and within said given area and located on a surface opposite to that containing said area, a second planar member fabricated from a second highly insulative material and coupled to said first planar member and having an aperture surrounding said given area, a third planar member fabricated from an insulative material and coupled to said second member, said third planar member having an aperture coaxial with and aligned with said first aperture, and having on a top surface thereof a series of terminal areas, and means coupling said piezoresistive sensor member to said terminal areas on said third planar member.

BRIEF DESCRIPTION OF THE FIGURES

FIG. 1 is a cross sectional view of a medical transducer according to this invention.

FIG. 2 is a top plan view of a ceramic plate utilized in the transducer.

FIG. 3 is a top plan view of a plate containing a gage arrangement for use in this invention.

FIG. 4 is a top plan view of a terminal format and circuitry on a ceramic substrate employed in this invention.

FIG. 5 is a longitudinal cross sectional view of an alternate transducer configuration.

FIG. 6 is a top plan view of a plate and diaphragm assembly employed with the transducer of FIG. 5.

DETAILED DESCRIPTION OF THE FIGURES

Referring to FIG. 1, there is shown a cross sectional view of a transducer assembly 10 particularly adapted for use in the medical field. FIG. 1 depicts a cross sectional view of the transducer assembly. Essentially, the transducer 10 has a rectangular configuration as will be explained although other geometrical configurations could be employed as well.

Referring to the Figure, there is shown a dome 11 or hemispherical housing having two pressure points 12 and 13 directed from the surface. Each pressure point as 12 and 13 communicates with the internal hollow of the dome. The port allows a tube to be coupled to a source of pressure fluid such as the blood stream of a patient while the other port allows the fluid to be recirculated back. The use of such domes with the associated pressure ports in regard to medical transducers is well known and such domes have been employed in the prior art. The dome is secured by means of an epoxy or other bond 15 to the surface of a ceramic rectangular plate 16.

The ceramic plate 16 may be fabricated from a conventional ceramic substance such as alumina. The plate 16 has a hole 18 through the surface thereof which hole communicates with the internal hollow of the dome 11. The ceramic plate 16 may be about 1/16 of an inch in thickness with the aperture 18 in the plate being about 0.4 inches in diameter.

Referring to FIG. 2, there is shown a top plan view of the ceramic plate 16 with the aperture 18.

Positioned above the plate 16 is a glass plate 17. The glass plate 17 is fabricated from a borosilicate glass as Pyrex, quartz or a glass which has a compatible thermal characteristic with respect to silicon. The glass plate 17 as indicated is relatively thin and serves as a diaphragm for a piezoelectric bridge 19 which is secured on the top surface of the thin plate 17. The glass plate 17 in bonded to the ceramic plate 16 by means of a soft material such as a medical grade RTV or silastic which are commercially available and employed to bond ceramic to glass or glass to glass. The semiconductor piezoelectric bridge 19 is electrostatically bonded to the top surface of the glass plate 17. Essentially, the electrostatic bonding process requires that the plate 17 and the bridge assembly 19 are heated and a bond is effected between the glass and silicon transducer by providing a a small current flow through the assembly by means of a power supply. The techniques for bonding the silicon assembly 19 to the glass plate 17 is sometimes referred to as anoidic bonding or electrostatic bonding.

For examples of such techniques, reference is made to U.S. Pat No. 3,951,707 entitled METHOD FOR FABRICATING GLASS BACKED TRANSDUCERS AND GLASS BACKED STRUCTURE issued on Apr. 20, 1976 to A. D. Kurtz, et al and assigned to the assignee herein. See also U.S. Pat. No. 3,868,719 entitled THIN RIBBON-LIKE GLASS BACKED TRANSDUCERS issued on Feb. 25, 1975 to A. D. Kurtz, et al and assigned to the assignee herein.

Positioned above the plate 17 is an additional glass plate 20. The glass plate 20 has an aperture 21 which surrounds the transducer gage assembly 19 and which serves to define the diaphragm area of the transducer. The aperture 21 is of a smaller diameter than aperture 18 and for example would be about 0.38 inches. The glass plate 20 is thicker than plate 17 and is approximately 0.062 inches in thickness. The plate 20 is further treated so that the under surface has deposited thereon a thin layer of silicon or other metallic or semiconducting material which may be deposited as by a vapor deposition technique. The plate 20 is then secured to plate 17 by means of an electrostatic bond as described above.

It is further understood that the plates 20 and 17 can be secured to each other by the use of a typical bonding agent such as an RTV.

Referring to FIG. 3, there is shown a top plan view of the plate 17 with a rectangular gage assembly 19. While the gage assembly may be secured to the glass plate 17 by means of electrostatic bonding, it is understood that the gage assembly may be directly deposited upon the glass plate 17 by means of the vapor deposition of silicon on plate 17 and the use of suitable masking techniques to fabricate the bridge structure.

The transducer consists of four elements each of which may be a piezoresistor and connected by four terminals such as 21 and 22. The piezoresistive element is conveniently fabricated monolithically in the form of an integral 4 arm bridge using transverse and longitudinal piezoresistive elements. Such a structure is typically 0.025 inches in width $\times$ 0.025 inches in length. Alternately, a shear gage configuration of similar dimensions may be employed. Such a sensor because of its mall size is very economical to fabricate by conventional bipolar type processing. Moreover, it makes maximum use of the strain at the edge of a small (0.33 inches) clamped edge diaphragm which is maximum at the edge but drops off very quickly. The small size of the gage employed contributes significantly to the low cost of the device and allows good signal from a diaphragm of convenient dimension.

The gages are arranged in a Wheatstone bridge configuration and may be a whole bridge or a half-bridge configuration. The terminals as 21 and 22 are metallized terminals and can have suitable leads bonded to the terminals by means of a ball bonding technique or other conventional integrated circuit techniques.

Positioned above the plate 20 is a top ceramic plate 25. The plate 25 has a small aperture 26 positioned over the gage area which is typically at the edge of the diaphragm active area. The top surface of plate 25 has positioned thereon the circuitry necessary for connecting the transducer assembly to the external environment. The plate 25 as indicated is fabricated from ceramic and is approximately 0.015 inches thick and is bonded to plate 20 by means of a soft bonding agent such as the trademarked product VITON or other suitable material such as RTV epoxy, etc.

Referring to FIG. 4, there is shown a top view of the plate 25. The leads as 30 and 31 which are coupled to the terminals of the gage configuration 19 are directed through aperture 26 to the top surface of the plate 25. The plate 25 contains a terminal pattern onto which the four leads emanating from the bridge are deposited. The pattern depicted on plate 25 may be imprinted thereon by thick film techniques which are widely employed in the ceramic art. The thick film techniques utilize conductive inks to provide the various electrical paths for the circuitry. The resistors as 27 and 28 are also positioned on the plate 25 and are used for span compensation and calibration techniques. The concept of compensating bridge circuits is well known in the art and reference can be made to various patents and other literature depicting such compensation techniques.

It should be noted that the transducer described has been conceived and executed using materials and fabrication processes such that very good uncompensated performance is achieved. Thus, the resistor network described is normally required only for zero balance and sensitivity adjustment. Thus a room temperature trim of the resistors by laser, sandblast trimmer or other means is all that is required to achieve performance as is normally required by the medical industry. This concept is important in achieving a low cost device suitable for use as a disposable transducer and along with other performance requirements dictated the structures herein described. The entire assembly is now placed in a plastic housing 40 where leads from terminal pads as 41 and 42 of the ceramic plate 25 are directed via cable 42 to be coupled to electrical monitoring equipment.

It should be noted that the dome 11 may be made an integral part of the plastic housing 40 where desirable for cost or other reasons. Although not shown, a cover would normally be employed to protect the resistor and gage areas to secure the cable. It should be noted that the mounting of the transducer structure to the plastic case is important to achieve isolation from case stress. The plastic case is normally desiged for maximum rigidity and the transducer structure is stiffened by the pressure of the relatively thick ceramic plates 16 and 20. Soft mounting such as RTV, VITRON or compliant type is employed to affix the transducer structure to the case.

It is important that the geometry of the interface between the dome and the diaphragm is well designed and controlled to prevent the formation of bubbles. Plate 16 can be eliminated to improve this interface in that regard and also to reduce the cost of the structure.

In regard to the above transducer, one will note that the various plates constituting the assembly are completely nonconductive as employing glass or ceramic. The patient is completely isolated from the gage 19 by means of the glass plate 17 which prevents any of the patient's fluid from contacting the gage and therefore minimizing the risk of having any current or voltage directed to the patient's body from the transducer assembly. The use of ceramic and glass in the techniques described above gives the entire assembly very high voltage isolation and therefore would prevent any high voltages generated by additional monitoring equipment from destroying the transducer or interfering with its operation.

In achieving the required isolation, the material and dimensions of the diaphragm must be carefully considered. It has been found that 0.010 inches of glass is necessary to achieve the typically required isolation of 10,000 VDC. This dictates a diaphragm of 0.38 inches diameter to achieve a suitable signal level based on the diaphragm edge strain. Glass is a particularly desirable material because of its low elastic modulus of 10 million psi. For instance, $Al_2O_3$ has a modulus of 50 million psi and an inconveniently large diaphragm would be required to achieve the same strain and isolation levels.

Referring to FIG. 5, there is shown an alternate structure with a dome 50 which basically serves the same function and purpose as dome 11 of FIG. 1. The dome 50 has two pressure ports 51 and 52 and is epoxy bonded to the surface of a glass plate 53. The glass plate 53 is fabricated from a 1/16 inch glass and essentially has a diaphragm area 54 formed by a depression in plate 53 and is shown in FIG. 6. The diameter of the depression 54 is 0.38 inches. Bonded to the glass plate is the strain gage configuration 55 which gage configuration may be electrostatically bonded or otherwise formed on the glass plate 53. Positioned above the glass plate 53 is a ceramic plate 56. Plate 56 has an aperture 57 which surrounds the gage pattern 55 and which is of a slightly larger diameter than the diameter of the recess 54. The ceramic plate 56 is bonded to plate 53 by means of an RTV or other soft material. Positioned above ceramic plate 56 is a second ceramic plate 57 of the exact configuration as plate 25 of FIG. 1.

The plate 57 has the terminal and circuit configuration as shown in FIG. 4 located thereon whereby the leads as 60 from the transducer structure can be coupled directly to the printed terminals on the ceramic plate 57 and thence directed via the cable 59 to the outside environment. The plate 56 is approximately 1/16 of an inch thick while plate 57 is 0.02 inches thick. The ceramic plate 56 is secured to plate 57 by means of VITON. Basically, VITON is a material used in the fabrication of O-rings and is quite well known. Again, both transducers depicted exhibit the same advantages. They are extremely simple to fabricate as the main components all exist and lie on rectangular shaped parts some of which have apertures and others circular depressions. It would be seen that this structure is very simple compared to the previously described structure and this is very economical to fabricate and thus is particularly suitable for a disposable transducer. Moreover, the plate 16 is not required in this structure which the diaphragm is kept well isolated from stress induced from the plastic case.

In this manner the shapes are very easy to machine and manufacture. Both transducer arrangements contain high insulative materials which substantially minimize the shock hazards of the transducer when employed in the medical environment. In both configurations, the strain gage or bridge is isolated from the patient's fluid passage by means of a glass barrier. The ceramic substrates assure that the transducer as well as the diaphragm is further isolated from the outside world and thus there is no conductive path through the layers which can couple to the patient or to the external monitoring equipment. The devices are extremely simple to manufacture and to use and based on their rectangular shape are easy to store.

By way of explanation, the approximate dimensions of each of the rectangular planar members such as the glass and the ceramic are approximately 1.26 inches in length and 0.6 inches in width. The transducer leads which emanate from the gage pattern 19 are coupled to the terminal areas on the ceramic board 25 by means of welding and/or conductive epoxy. The resistors may be discrete devices of the integrated circuit type which are positioned on the substrate 25 or may be directly formed during the thick film printing of the circuit pattern on the board 25. An active laser trim at room temperature is the most effective and economical way of adjusting the transducer. Essentially, the transducer with the above noted dimensions will operate at pressures up to about 6 psi but can experience overload pressures in excess of 80 psi and handle voltage transients up to 10,000 volts without being destroyed. The structure then meets the above requirements by means of careful dimensional choices and the use of the proper diaphragm material. The modules as above described are interchangeable in a wide variety of products. The glass layer as indicated is used for voltage isolation and for protection in general.

While the ceramic may be conveniently fabricated from alumina, other materials such as steritate, sapphire, spinel, berrylium and other types of ceramic materials can be employed as well. By the combination of the ceramic technology with glass technology, one eliminates many complicated steps found in the manufacture and production of similar types of transducers which enable this transducer to be produced and manufactured economically. The dome is fabricated from a typical nonreactive plastic as one of many which are used in the medical field as Mylar.

In regard to the manufacture of the above noted devices, the preferably technique is to first electrostatically bond the diaphragm member 17 of FIG. 1 to the aperture glass plate 20. After this step, the gage 19 would be bonded within the aperture 21 and the top ceramic plate 25 would be secured to the glass plate by means of an RTV compound.

Leads would be attached to the gage and directed to the terminal areas on the ceramic substrate 25. The bottom ceramic plate 16 which also may be made of glass or plastic would be coupled to the diaphragm plate 17 and the dome would be epoxied to the ceramic. The unit would then be placed in the plastic housing and the cable as 42 or 59 would be attached.

We claim:

1. A pressure transducer apparatus particularly adapted for use in implementing pressure measurements in the medical field comprising:
   a planar member fabricated from a highly insulative material and having on a surface a given area adapted to deflect upon application of a force thereto;
   a dome member having an opened bottom and a domed surface with a hollow between said opened bottom and said domed surface with said opened bottom coupled about said given area of said planar member, with said dome member having at least one pressure port extending from said domed surface and communicating with said hollow,
   a piezoresistive sensor member secured to said planar member and within said given area,
   a terminal planar member fabricated from an insulative material and coupled to said planar member, said terminal planar member having an aperture aligned with said active area, and having on a top surface thereof a series of terminal areas, and means coupled said piezoresistive sensor member to said terminal areas on said terminal planar member.

2. The pressure transducer according to claim 1, wherein said planar member is a rectangular member fabricated from ceramic and having a depression on a surface indicative of said given area.

3. The pressure transducer according to claim 1, wherein said planar member is a composite member comprising a first glass planar member of a given thickness secured to a thinner glass planar member with said planar member having an aperture indicative of said given area.

4. The pressure transducer according to claim 1, wherein said terminal planar member is fabricated from a ceramic material.

5. The pressure transducer according to claim 1, wherein said piezoresistive sensor member is a bridge array bonded to said planar member by an electrostatic bond.

6. The pressure transducer according to claim 1, wherein said dome member is coupled to said planar member by means of an epoxy.

7. The pressure transducer according to claim 1, further including a plastic housing secured about said planar members for containing the same.

8. A pressure transducer, comprising;
   a first planar member fabricated from a ceramic material and having an aperture located on a surface thereof,
   a second planar member secured in congruency to said first member, said second member fabricated from glass and being relatively thin as compared to said first member,
   a semiconductor gage configuration bonded to said second member at the surface opposite to the surface secured to said first member,
   a third glass planar member secured in congruency to said second planar member at said opposite surface and having an aperture for surrounding said gage configuration,
   a fourth ceramic planar member secured to said third glass member and having an aperture coaxial with said aperture in said third member, said fourth ceramic member having terminal paths on a surface opposite to the surface secured to said third planar member, and means coupling said gage configuration to said terminal paths on said fourth planar member.

9. The pressure transducer according to claim 8, wherein said second and third members are secured together by an electrostatic bond.

10. The pressure transducer according to claim 8, further including a hemispherical hollow dome assembly having an opened bottom and at least one pressure port extending from said dome, with said opened bottom secured about said aperture in said first planar member.

11. The pressure transducer according to claim 8, wherein said dome is secured to said first planar member by means of an epoxy.

12. The pressure transducer according to claim 8, wherein said planar members are rectangular in configuration.

13. A pressure transducer comprising:
   a first planar glass member having located on a surface thereof a depression,
   a second planar ceramic member secured in congruency with said first member at the surface opposite to that containing said depression, said second member having an aperture of a given diameter coaxially aligned with said depression, a piezoresistive gage bonded to said first member at said surface secured to said second member and located so as to be surrounded by said aperture,
   a third planar ceramic member having an aperture coaxial with said aperture in said second planar member and bonded at a surface to said second planar member, with the surface opposite said bonded surface having a plurality of interconnection paths and areas coupling said gage to said interconnection paths.

14. The pressure transducer according to claim 13, further comprising a pressure receiving dome having an opened bottom bonded about said depression in said first planar member and having a pressure input port.

15. The pressure transducer according to claim 13, wherein said planar members are rectangular in configuration.

16. The pressure transducer, according to claim 13, wherein said first planar member is secured to said second planar member by means of an RTV.

17. The pressure transducer according to claim 13, wherein said piezoresistive gage is electrostatically bonded to said second planar member.

18. A pressure transducer apparatus particularly adapted for use in implementing pressure measurements in the medical field, comprising;
- a first planar member fabricated from a first highly insulative material and having on a surface a given area adapted to deflect upon application of a force thereto;
- a hemispherical hollow member having an opened bottom and a domed surface with said opened bottom coupled about said given area of said first planar member, with said hemispherical member having at least one pressure port extending from said domed surface and communicating with said hollow,
- a piezoresistive sensor member secured to said first planar member and within said given area and located on a surface opposite to that containing said area,
- a second planar member fabricated from a second highly insulative material and coupled to said first planar member and having an aperture surrounding said given area,
- a third planar member fabricated from an insulative material and coupled to said second member, said third planar member having an aperture coaxial with and aligned with said first aperture, and having on a top surface thereof a series of terminal areas, and means coupling said piezoresistive sensor member to said terminal areas on said third planar member.

19. The pressure transducer according to claim 18, wherein said second planar member is fabricated from a glass material.

20. The pressure transducer according to claim 18, wherein said third planar member is fabricated from a ceramic material with said terminal areas printed thereon by a thick film technique.

* * * * *